United States Patent [19]

DeWilde et al.

[11] 4,420,255

[45] Dec. 13, 1983

[54] ADIABATIC BURNER FOR PREMIXED GASES

[75] Inventors: Mark A. DeWilde, Forest Hill; Richard A. Beyer, Baltimore, both of Md.

[73] Assignee: The United States of America as represented by the Secretary of the Army, Washington, D.C.

[21] Appl. No.: 302,892

[22] Filed: Sep. 16, 1981

[51] Int. Cl.³ .......................... G01J 3/30; G01N 21/72
[52] U.S. Cl. .................................... 356/315; 431/126; 422/54; 436/35; 436/154
[58] Field of Search ....................... 356/315, 417, 318; 431/4, 126; 422/54; 436/35, 154; 239/75, 601

[56] References Cited

U.S. PATENT DOCUMENTS 3,469,794  9/1969  Hell .............................. 356/417 X
3,516,771  6/1970  Rendina ........................ 356/315 X

OTHER PUBLICATIONS

Stephenson, "Non-Intrusive Profiles of Atmospheric Premixed Hydrocarbon-Air Flames", 17th Symposium (International) on Combustion, Leeds, England pp. 993-999 (1978).

Beyer et al., "Raman Spectroscopy of premixed Ch4/N2O Flames", CPIA Publication 329 of The 17 Jannax Combustion Meeting, Nov. 1980, pp. 391-399.

Gogvel, "An Improved Nitrous Oxide Burner for Atomic Absorption spectroscopy", New Zealand Journal of Science, vol. 13, #4, Dec. 1970.

Primary Examiner—F. L. Evans
Assistant Examiner—L. A. Dietert
Attorney, Agent, or Firm—Robert P. Gibson; Anthony T. Lane; A. Victor Erkkila

[57] ABSTRACT

A research type burner is provided which permits ready optical access for study of precombustion and primary reaction zones of adiabatic flames of premixed gases. The burner includes a channel for relatively laminar gas flow having an outlet with a pair of essentially parallel closely spaced knife edges for providing an essentially stable and adiabatic flame. The knife edges project sufficiently above the burner housing to allow the passage of a laser beam between the knife edges through the zone to be studied.

5 Claims, 6 Drawing Figures

ity. Also, it avoids questions as to the validity of applying low pressure measurements to atmospheric or higher pressures, since the chemical pathways may change with pressure conditions due to differences in heat transport and other effects. Further, the flame is essentially adiabatic because the knife edges of the burner extract only very small amounts of heat from the flame, so that the flames under study are easier to compare with detailed numerical models. The burner of the present invention can also achieve hotter flame temperatures, which provide an improved source of free radicals for spectroscopic study thereof, since the increased temperatures produce up to several orders of magnitude more free radicals as compared to conventional one-dimensional flame burners when operated at atmospheric pressure. Also, the novel burner is of relatively simple, inexpensive design, which can be readily fabricated without the use of sophisticated tools.

ADIABATIC BURNER FOR PREMIXED GASES

GOVERNMENT RIGHTS

The invention described herein may be manufactured, used and licensed by the Government for Government purposes without the payment to us of any royalty thereon.

BACKGROUND OF THE INVENTION—PRIOR ART

The present invention relates to gas burners and, in particular, to a burner for research purposes, which permits ready optical study of the pre-combustion and primary reaction zones of adiabatic flames of combustible gas mixtures.

The reaction chemistry of flames has been the subject of considerable investigation. These investigations have generally focused attention on the thin primary reaction zone, which is typically of the order of 100 um thick for a near stoichiometric flame at atmospheric pressure. Burners employed in the past for studying these systems have generally utilized an array of tubes or the like, sintered porous metal disks, a metal screen or plate, or some other physical barrier to establish a stable flame. All of these methods and devices result in extraction of heat from the flame, the amount dependent upon several physical parameters. In a typical configuration, a stable flame requires that the primary reaction zone be seated on the burner surface; however, this position renders access to the primary reaction zone quite difficult at atmospheric pressure. Low presure chambers have been frequently used to expand the flame zones.

A burner useful for laser probing of flame systems has been recently developed. The burner utilizes a knife edge and a precision machined surface to provide a non-adiabatic flame which can be studied by laser spectroscopy through the primary reaction zone. (D. A. Stephenson, "Non-Intrusive Profiles of Atmospheric Premixed Hydrocarbon-Air Flames:, 17th Symposium (International) on Combustion, Leeds, England, P. 993, 1978).

Accordingly, There is a need for a research type burner which permits ready optical access to the pre-combustion and primary reaction zones of adiabatic flames of combustible gas mixtures.

SUMMARY OF THE INVENTION

In accordance with this invention there is provided a burner having a channel providing relatively laminar flow of a combustible gas mixture and having an outlet with a pair of essentially parallel knife edges for aerodynamic stabilization of a flame, which is essentially adiabatic. The knife edges project sufficiently above any other element of the burner to allow the passage of a laser beam between said knife edges so that the beam can pass below or through any part of the primary reaction zone to be studied.

The research burner of the present invention provides an adiabatic, approximately one-dimensional flame which is accessible for laser probing of the temperature or chemical composition through much of the preheat (precombustion) region, where the temperature of the reactant gases rises but no chemical reactions take place, and all of the primary reaction zone, using stoichiometric mixtures at atmospheric pressure. The novel burner eliminates the use of a low pressure chamber, and hence results in much greater experimental simplicity. Also, it avoids questions as to the validity of applying low pressure measurements to atmospheric or higher pressures, since the chemical pathways may change with pressure conditions due to differences in heat transport and other effects. Further, the flame is essentially adiabatic because the knife edges of the burner extract only very small amounts of heat from the flame, so that the flames under study are easier to compare with detailed numerical models. The burner of the present invention can also achieve hotter flame temperatures, which provide an improved source of free radicals for spectroscopic study thereof, since the increased temperatures produce up to several orders of magnitude more free radicals as compared to conventional one-dimensional flame burners when operated at atmospheric pressure. Also, the novel burner is of relatively simple, inexpensive design, which can be readily fabricated without the use of sophisticated tools.

BRIEF DESCRIPTION OF THE DRAWINGS

The above brief description as well as other objects, features and advantages of the present invention will be more fully appreciated by reference to the following detailed description of a presently preferred but nonetheless illustrative embodiment in accordance with the present invention when taken in conjunction with the accompanying drawings wherein.

DETAILED DESCRIPTION OF THE PREFERRED EMBODIMENT

Figure 1:
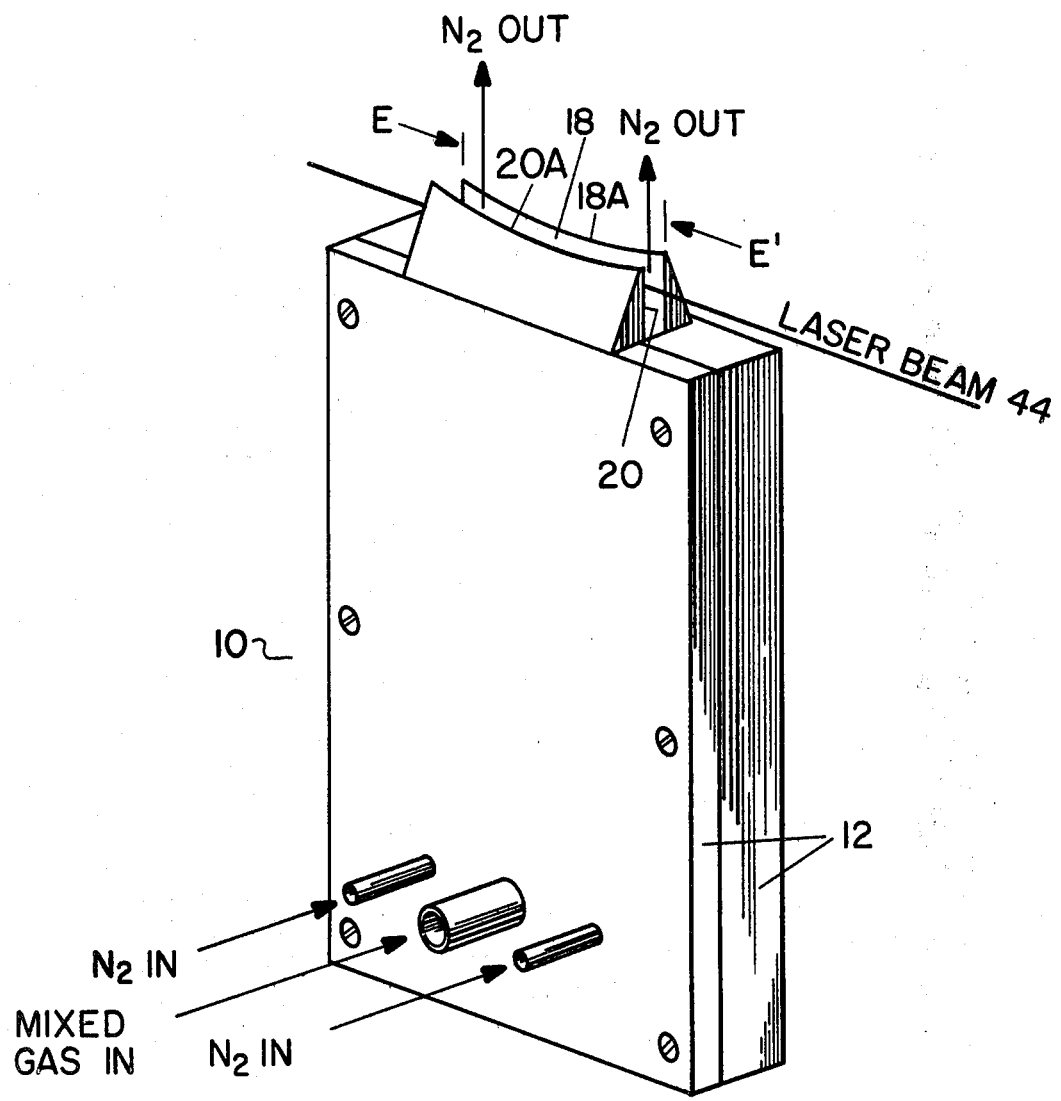
FIG. 1 is an idealized perspective view of a burner according to the principles of the present invention illustrating the manner of probing the gas outlet with a laser beam.
Figure 2:
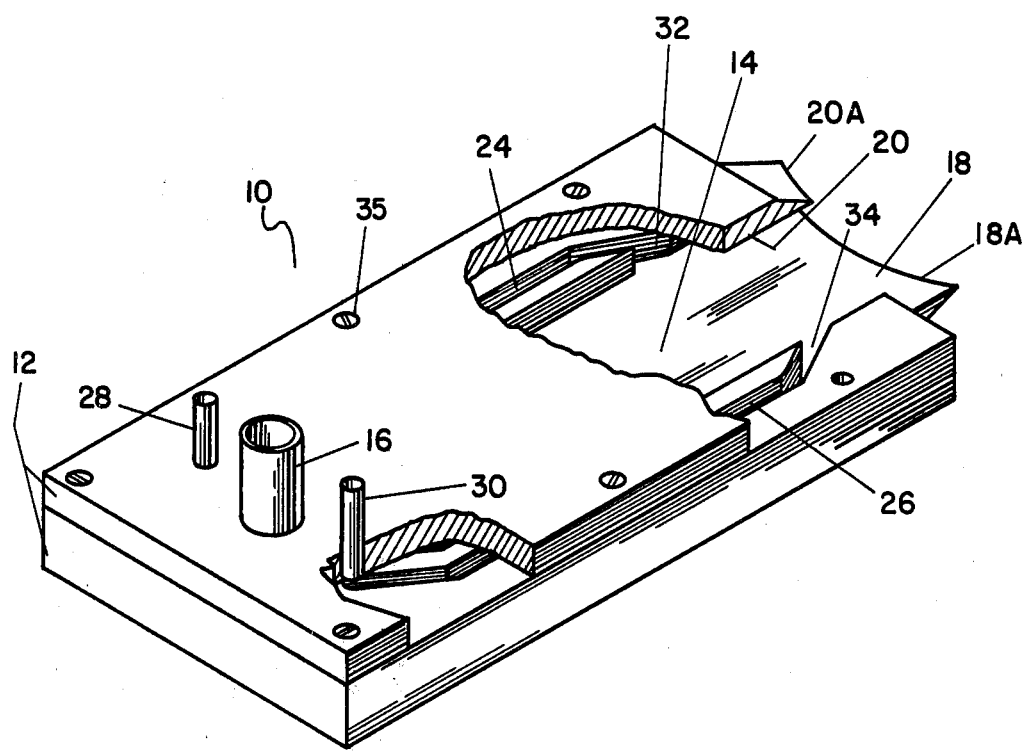
FIG. 2 is a partially sectioned view of a burner similar to that shown in FIG. 1 made by bolting together the plates shown in FIGS. 2A and 2B.

Referring to FIGS. 1, 2, 2A and 2B, a burner 10 is shown which has a housing 12 containing a channel 14 which provides a uniform confined gas flow and is typically rectangular in cross section. The channel is provided with an inlet port 16 for entering the premixed gases and an outlet having a pair of parallel walls 18 and 20 containing knife edges 18A and 20A for exiting the gas mixture into the atmosphere for burning. As shown in FIGS. 1 and 2, the outlet containing the knife edges and open sides projects above the body of the burner housing sufficiently so that a laser beam can be passed well below the flame reaction zone between the outlet walls/knife edges parallel to the top of the burner housing. Conduits 24 and 26 having inlet ports 28 and 30 are provided for passing a moderate flow of an inert gas, such as nitrogen, to the ends 32 and 34 of channel 14, such flow serving to turn upward the ends of the flame to minimize disturbance of an optical probe beam as it enters the channel between said knife edges.

Figure 2A:
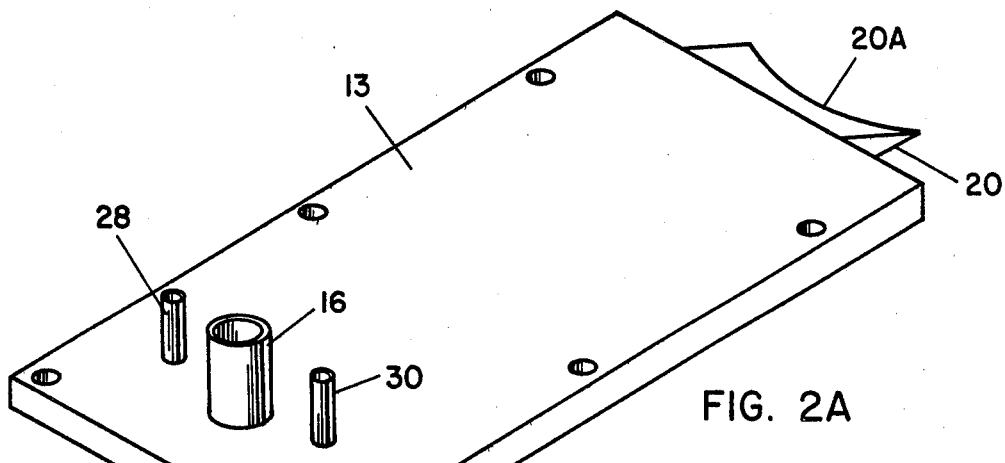
Figure 2B:
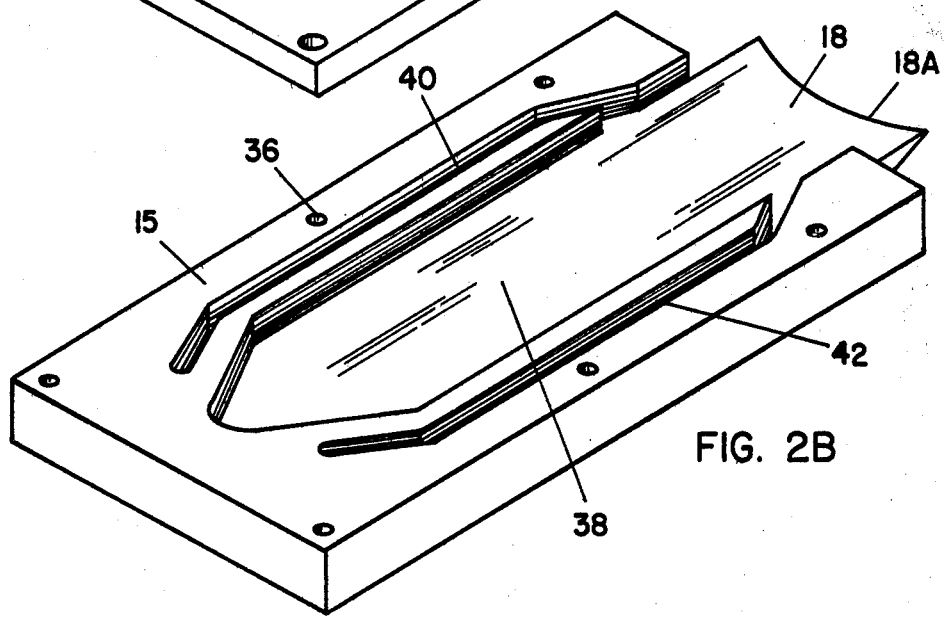
Figure 3:
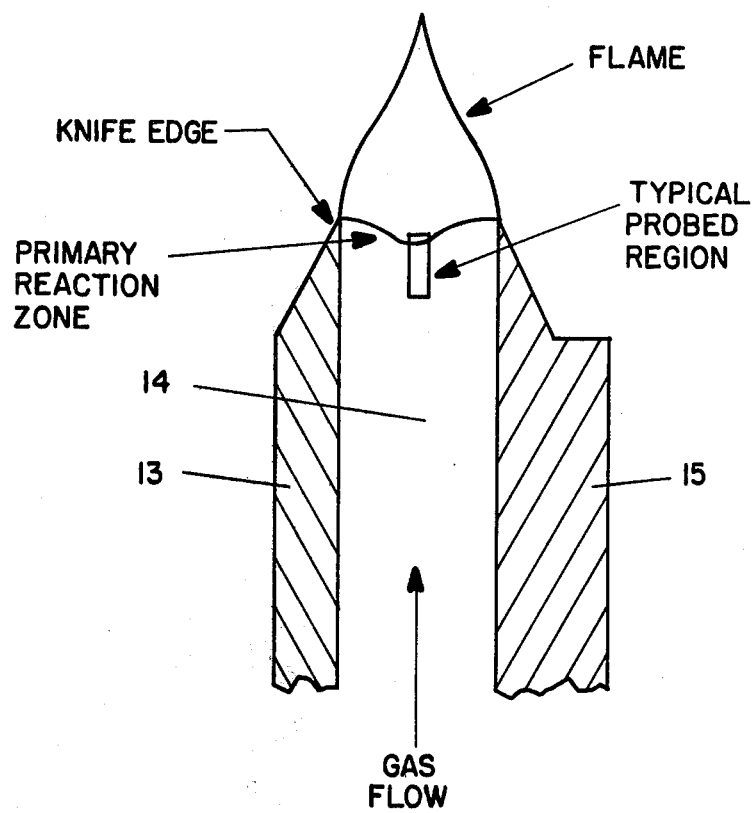
FIG. 3 is a cross-section view showing the knife edges, flame and primary reaction zone and optical probe region of the burner according to the present invention.

The burner shown in FIG. 2 can be readily made by mounting the plate 13, shown in FIG. 2A on the plate 15 shown in FIG. 2B with screws 35 inserted through holes 36. The plate 15 of FIG. 2B contains a wide flat groove 38 and narrow grooves 40 and 42, while the plate 13 of FIG. 2A contains inlet ports 16, 28 and 30. When the plates are screwed together, groove 38 forms channel 14 and narrow grooves 40 and 42 form conduits 24 and 26 in the resulting burner shown in FIG. 2.

In operation, a stream of premixed gases is introduced via inlet port 16, flows through channel 14, and exits via the outlet containing knife edges 18A and 20A into the atmosphere where it is flamed, the flame being stabilized on said knife edges. A moderate flow of inert gas is simultaneously introduced via inlet ports 28, 30 and flows through conduits 24, 26 to the ends 32, 34 of channel 14 to turn the ends of the flame upward and minimize disturbance of the laser beam. As shown in FIG. 1, a laser beam 44 is passed through the channel between the outlet walls with knife edges to measure the temperature and/or concentration of chemical constituents of the flame system in accordance with known spectroscopic techniques.

The essential novel elements of the burner of the present invention include a channel for providing a relatively laminar flow of the combustible gas mixture, and an outlet having knife edges for aerodynamic stabilization of an essentially adiabatic flame. The flame is essentially adiabatic, since the knife edges of the burner extract only very small quantities of heat from the flame. Channel outlets containing a pair of closely spaced, essentially parallel and coextensive walls terminating in knife edges, wherein the outlet channel between the walls 18 and 20 and knife edges 18A and 20A ranges about from 25 mm to 50 mm in length, as measured between the ends E and $E_1$ of the walls/knife edges, and the knife edges are separated by about from 1 to 3 mm, have been satisfactorily employed in a burner according to the present invention, although the invention is not limited to these dimensions. In general, the channel is of rectangular cross-section. Also, the channel walls are preferably coplanar and integral with the outlet walls containing the pair of knife edges, as illustrated in FIGS. 2, 2A and 2B. Copper, aluminum and brass can be suitably employed for constructing the burner components including the channel walls, knife edges, housing, etc.

The flow in the burner of the present invention is that of a pure jet or momentum plume (R. S. Scorer, International Series of Monographs in Aeronautics and Astronautics Div. 2: Aerodynamics Vol. 1, Natural Aerodynamics, page 186. Published by McMillan Company New York, N.Y. 1958.) Thus, a good laminar flow of the gases and a flame which fills the total length of the channel can be obtained by keeping the included angle between the ends of the knife edges 18A and 20A with the apex at the mixed gas inlet 16 equal to 24° or less, i.e. the length of flow should be approximately two and a half times the length of the flame at the knife edges 18A and 20A.

The following examples illustrate the use of a burner shown in the figures and described above to measure temperature profiles through the primary reaction zones of two flame systems at atmospheric pressure.

EXAMPLE 1

$CH_4/N_2O$ Mixture With $N_2$ Diluent

The conditions were as follows:
a. The knife edges were separated by 1.5 mm., and the length of the channel between the knife edges was 50.8 mm.
b. The flow rates were:
$N_2O$ 0.61 liter/min.
$CH_4$ 0.25 liter/min.
$N_2$ 0.23 liter/min.

Figure 4:
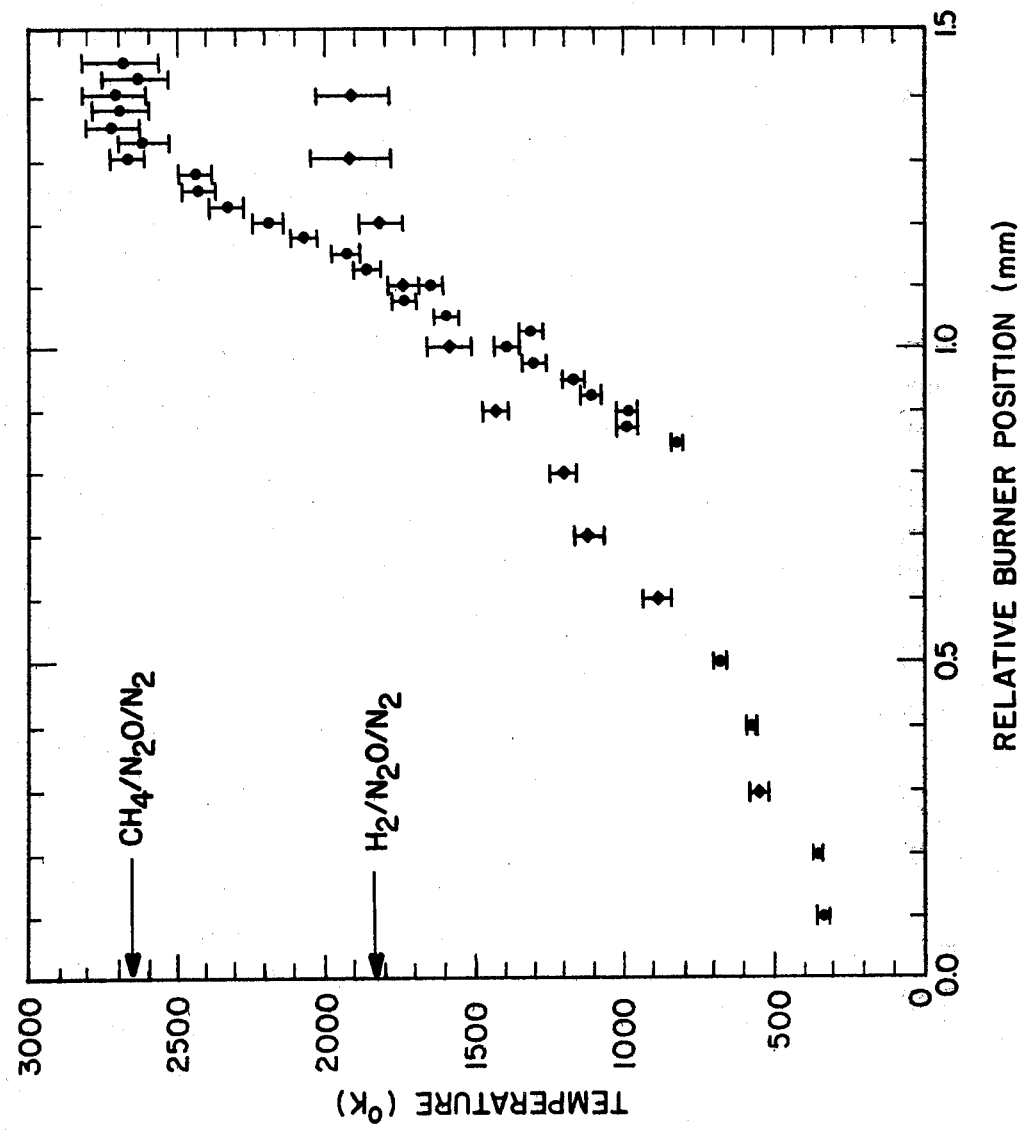
FIG. 4 is a graph showing the temperature profiles for flames of a $CH_4/N_2O$ mixture and a $H_2/N_2O$ mixture measured using a burner of the present invention.

The calculated stoichiometry from these numbers is $\phi = 1.6$ (fuel rich). The calculated adiabatic temperature for this mixture is 2655 K. as shown in FIG. 4. The temperatures were calculated by using a multi-parameter least squares fitting of the nitrogen ($N_2$) Q-branch rotational-vibrational Raman spectrum to synthetic spectra.

EXAMPLE 2

$H_2/N_2O$ Mixture With $N_2$ Diluent

The following conditions were employed:
a. The knife edges were separated by 3 mm. and the length of the channel between the knife edges was 50.8 mm.
b. The gas proportions were:
$N_2$ 47%
$H_2$ 37%
$N_2O$ 16%

The calculated stoichiometry is $=2.3$. The flow rates were not measured. The temperatures shown in FIG. 4 were calculated from the relative peak heights of up to six rotational peaks of the Q-branch of the $H_2$ rotational-vibrational Raman spectrum via least squares fits to the Boltzmann equation. FIG. 4 shows the temperature profiles for the flames of the gas mixtures of examples 1 and 2 measured through the primary reaction zone on the knife edge burner, wherein the $CH_4/N_2O$ mixture is indicated by ⊙ and the $H_2/N_2O$ mixture is indicated by ◇. The adiabatic flame temperatures for these mistures are also indicated in FIG. 4.

Measurements of species concentrations (e.g. chemical constituents, free radicals, etc.) of these flame systems can be accomplished by use of known spectroscopic techniques.

The foregoing disclosure and drawings are merely illustrative of the principles of this invention and are not to be interpreted in a limiting sense. We wish it to be understood that we do not desire to be limited to the exact details of construction shown and described because obvious modifications will occur to a person skilled in the art.

We claim:

1. A method for optically probing the precombustion and primary reaction zones of an essentially adiabatic flame of a combustible gas mixture, which comprises introducing a stream of said gas mixture into a burner channel having an outlet including a pair of essentially parallel and coextensive walls each terminating in a knife edge, passing said gases through said channel under relatively laminar flow conditions, flaming said gas mixture exiting said outlet, and passing an optical probe between said outlet walls with knife edges through said precombustion or primary reaction zones of a flame of said combustible gas mixture, said knife edges providing a stable, essentially adiabatic flame where the combustible gas mixture exits said outlet.

2. A method according to claim 1, wherein the channel walls are integral and coplanar with said knife edge walls.

3. A method according to claim 1, wherein an inert gas is introduced into the ends of said outlet for turning the ends of the flame upward.

4. A method according to claim 1, wherein the optical probe is a laser beam.

5. A method according to claim 1 or 2, wherein the parallel knife edges are spaced apart by about from 1 mm to 3 mm.

* * * * *